(12) United States Patent
Kerns et al.

(10) Patent No.: US 12,179,015 B2
(45) Date of Patent: Dec. 31, 2024

(54) BIOSTIMULATOR TRANSPORT SYSTEM HAVING WELDLESS BEARING RETAINER

(71) Applicant: Pacesetter, Inc., Sylmar, CA (US)

(72) Inventors: Scott Kerns, Cologne, MN (US);
Daniel Goodman, Minnetonka, MN (US); Adam Weber, Minnetonka, MN (US)

(73) Assignee: PACESETTER, INC., Sylmar, CA (US)

( * ) Notice: Subject to any disclaimer, the term of this patent is extended or adjusted under 35 U.S.C. 154(b) by 0 days.

(21) Appl. No.: 17/991,393

(22) Filed: Nov. 21, 2022

(65) Prior Publication Data

US 2023/0081021 A1    Mar. 16, 2023

Related U.S. Application Data

(63) Continuation of application No. 16/838,865, filed on Apr. 2, 2020, now Pat. No. 11,504,528.

(Continued)

(51) Int. Cl.
*A61B 17/34* (2006.01)
*A61M 25/00* (2006.01)
(Continued)

(52) U.S. Cl.
CPC .......... *A61N 1/057* (2013.01); *A61B 17/3468* (2013.01); *A61M 25/0067* (2013.01);
(Continued)

(58) Field of Classification Search
CPC ............... A61N 1/372; A61B 17/3468; A61M 25/0067; A61M 25/0147
See application file for complete search history.

(56) References Cited

U.S. PATENT DOCUMENTS

| 4,687,365 A | * | 8/1987 | Promersberger | ........ F16G 15/08 411/395 |
| 4,765,762 A | * | 8/1988 | Rozentals | ............... F16C 19/16 384/510 |

(Continued)

OTHER PUBLICATIONS

Invitation to Pay Additional Fees and Where Applicable, Protest Fee; International Application No. PCT/US2020/026942 dated Jul. 31, 2020; 9 pages.

(Continued)

*Primary Examiner* — Eric D. Bertram
(74) *Attorney, Agent, or Firm* — WOMBLE BOND DICKINSON (US) LLP

(57) ABSTRACT

A transport system for delivery or retrieval of a biostimulator, such as a leadless cardiac pacemaker, is described. The biostimulator transport system includes a docking cap supported by a bearing within a bearing housing. The bearing allows relative rotation between a torque shaft connected to the docking cap and an outer catheter connected to the bearing housing. The bearing housing and the docking cap include respective bearing retainers that constrain the bearing within the bearing housing without a weld attachment. The weldless retainers of the biostimulator transport system provide a robust mechanical securement of the bearing that is not vulnerable to corrosion. Other embodiments are also described and claimed.

19 Claims, 8 Drawing Sheets

Related U.S. Application Data

(60) Provisional application No. 62/843,126, filed on May 3, 2019.

(51) Int. Cl.
*A61M 25/01* (2006.01)
*A61N 1/05* (2006.01)
*A61N 1/372* (2006.01)
*A61N 1/375* (2006.01)

(52) U.S. Cl.
CPC .... *A61M 25/0082* (2013.01); *A61M 25/0147* (2013.01); *A61N 1/372* (2013.01); *A61N 2001/0578* (2013.01); *A61N 1/37512* (2017.08); *A61N 1/3756* (2013.01)

(56) References Cited

U.S. PATENT DOCUMENTS

| | | | |
|---|---|---|---|
| 6,389,320 B1 | 5/2002 | Pianca | |
| 9,126,032 B2* | 9/2015 | Khairkhahan | A61N 1/3756 |
| 10,188,425 B2* | 1/2019 | Khairkhahan | A61B 17/221 |
| 10,448,973 B2* | 10/2019 | Arnar | A61B 17/32053 |
| 10,518,095 B2* | 12/2019 | Ho | A61N 1/3756 |
| 11,058,457 B2* | 7/2021 | Khairkhahan | A61N 1/3756 |
| 11,504,528 B2* | 11/2022 | Kerns | A61M 25/0147 |
| 2004/0046440 A1* | 3/2004 | Brinker | F16D 65/12 |
| | | | 301/105.1 |
| 2007/0044530 A1* | 3/2007 | Grogan | B21D 51/2615 |
| | | | 72/126 |
| 2008/0131046 A1* | 6/2008 | Weier | F16C 35/067 |
| | | | 384/589 |
| 2015/0051615 A1 | 2/2015 | Schmidt et al. | |
| 2016/0067446 A1* | 3/2016 | Klenk | A61N 1/3756 |
| | | | 606/129 |
| 2017/0312479 A1 | 11/2017 | Keaveney et al. | |
| 2017/0340877 A1* | 11/2017 | Ollivier | A61N 1/3756 |
| 2018/0104451 A1* | 4/2018 | Kerns | A61N 1/37512 |
| 2018/0104452 A1* | 4/2018 | Goodman | A61M 25/0147 |
| 2018/0303513 A1* | 10/2018 | Kerns | A61N 1/37512 |
| 2019/0110812 A1* | 4/2019 | Khairkhahan | A61B 17/3468 |
| 2020/0101299 A1* | 4/2020 | Arnar | A61B 17/3439 |
| 2020/0345396 A1* | 11/2020 | Rickheim | A61B 17/3468 |
| 2021/0298788 A1* | 9/2021 | Khairkhahan | A61N 1/3756 |
| 2023/0140405 A1* | 5/2023 | Wheeler | B62D 55/125 |
| | | | 74/405 |

OTHER PUBLICATIONS

PCT International Search Report and Written Opinion from related PCT Application No. PCT/US2020/026942, mailed Sep. 25, 2020, 14 pages.
PCT International Preliminary Report on Patentability from related PCT Application No. PCT/US2020/026942, mailed Nov. 18, 2021, 10 pages.
First Office Action from related Chinese Patent Application No. 202080031820.0 mailed on Jan. 3, 2024 (9 pages including translation).
Extended European Search Report from related EP Application No. 24174711.2 mailed on Sep. 10, 2024, 6 pages.

* cited by examiner

BIOSTIMULATOR TRANSPORT SYSTEM HAVING WELDLESS BEARING RETAINER

This application is a continuation of U.S. patent application Ser. No. 16/838,865, filed on Apr. 2, 2020, now U.S. Pat. No. 11,504,528, which claims the benefit of priority of U.S. Provisional Patent Application No. 62/843,126, filed on May 3, 2019, titled "Biostimulator Transport System Having Weldless Bearing Retainer," and these applications are incorporated herein by reference in their entirety to provide continuity of disclosure.

BACKGROUND

Field

The present disclosure relates to biostimulators and related delivery and retrieval systems and methods. More specifically, the present disclosure relates to transport systems for delivery or retrieval of leadless biostimulators.

Background Information

Cardiac pacing by an artificial pacemaker provides an electrical stimulation of the heart when its own natural pacemaker and/or conduction system fails to provide synchronized atrial and ventricular contractions at rates and intervals sufficient for a patient's health. Such antibradycardial pacing provides relief from symptoms and even life support for hundreds of thousands of patients. Cardiac pacing may also provide electrical overdrive stimulation to suppress or convert tachyarrhythmias, again supplying relief from symptoms and preventing or terminating arrhythmias that could lead to sudden cardiac death.

Cardiac pacing by currently available or conventional pacemakers is usually performed by a pulse generator implanted subcutaneously or sub-muscularly in or near a patient's pectoral region. The generator usually connects to a proximal end of one or more implanted leads, the distal end of which contains one or more electrodes for positioning adjacent to the inside or outside wall of a cardiac chamber. Although more than one hundred thousand conventional cardiac pacing systems are implanted annually, various well-known difficulties exist, of which a few will be cited. For example, a pulse generator, when located subcutaneously, presents a bulge in the skin that patients can find unsightly, unpleasant, or irritating, and which patients can subconsciously or obsessively manipulate or "twiddle." Even without persistent manipulation, subcutaneous pulse generators can exhibit erosion, extrusion, infection, disconnection, insulation damage, or conductor breakage at the wire leads. Although sub-muscular or abdominal placement can address some concerns, such placement involves a more difficult surgical procedure for implantation and adjustment, which can prolong patient recovery.

Leadless cardiac pacemakers incorporate electronic circuitry at the pacing site and eliminate leads, and thus, avoid the above-mentioned shortcomings of conventional cardiac pacing systems. Leadless cardiac pacemakers can be anchored at the pacing site by an anchor. During delivery or retrieval of a leadless cardiac pacemaker, a transport system can apply torque to the leadless cardiac pacemaker via a docking cap to screw the anchor into, or out of, the target tissue.

SUMMARY

Existing transport systems used for delivery or retrieval of leadless cardiac pacemakers may have a deflectable catheter, and a deflection mechanism of the deflectable catheter can impart stress to an attachment between the docking cap and the deflectable catheter. Such stress may induce mechanical failure of the transport system, e.g., at a bearing that connects the docking cap to the deflectable catheter. Existing modes of securing the bearing to the docking cap include welds, which are susceptible to corrosion and mechanical weakness because the bearing and docking cap are typically made from different materials. Accordingly, biostimulator transport systems would benefit from mechanisms of securing the bearing to the docking cap that are mechanically robust and reduce a likelihood of corrosion.

A biostimulator transport system, such as a catheter-based system for delivering or retrieving a leadless cardiac pacemaker, having a weldless bearing retention mechanism and a deflection mechanism contained within a bearing housing, is provided. In an embodiment, the biostimulator transport system includes an outer catheter and a torque shaft extending through an inner lumen of the outer catheter. More particularly, a bearing housing is mounted on a distal end of the outer catheter, and a docking cap is mounted on a distal end of the torque shaft. The docking cap can rotate relative to the bearing housing. A bearing is radially between the bearing and the docking cap to support such rotation. For example, an outer wall of the bearing, e.g., of an outer ball bearing race, can appose the bearing housing, and an inner wall of the bearing, e.g., of an inner ball bearing race, can appose the docking cap.

The bearing housing can include an outer bearing retainer and the docking cap can include an inner bearing retainer, and the bearing retainers can be longitudinally on opposite sides of the bearing to retain the bearing in a longitudinal direction. For example, the inner bearing retainer can have a distal retainer face apposed to a proximal bearing face of the bearing, and the outer bearing retainer can have proximal retainer face apposed to a distal bearing face of the bearing. The retainer faces can interfere with longitudinal movement of the retainer to keep the retainer in place without the need for welds between the bearing and the docking cap or the bearing housing.

In an embodiment, the inner bearing retainer includes an inner annulus mounted on a neck of the docking cap, and the outer bearing retainer includes an outer annulus coupled to a distal flange of the bearing housing. The annuluses can provide the bearing retainers to constrain the bearing without being directly attached to the bearing. Accordingly, the biostimulator transport system can include a weldless bearing retainer to constrain a bearing that permits rotation between a torque shaft and an outer catheter. The bearing requires no welds to the docking cap or the bearing housing, and thus, the bearing retention mechanism is mechanically robust and reduces a likelihood of corrosion.

The above summary does not include an exhaustive list of all aspects of the present invention. It is contemplated that the invention includes all devices, systems, and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Embodiments describe a biostimulator transport system, e.g., a catheter-based system for delivery or retrieval of a leadless cardiac pacemaker, having a weldless bearing retainer. The biostimulator may be used to pace cardiac tissue as described below. The biostimulator, however, may be used in other applications, such as deep brain stimulation, and thus, reference to the biostimulator as being a cardiac pacemaker is not limiting.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator transport system. Similarly, "proximal" may indicate a second direction opposite to the first direction. Such terms are provided to establish relative frames of reference, however, and are not intended to limit the use or orientation of a biostimulator transport system to a specific configuration described in the various embodiments below.

In an aspect, a biostimulator transport system is provided. The biostimulator transport system includes a bearing radially between a bearing housing and a docking cap, and the bearing is not secured to the bearing housing or the docking cap by a weld. For example, the bearing can be axially between respective bearing retainers of the bearing housing and the docking cap. Weldless securement of the bearing allows the bearing to support relative rotation of the components with less vulnerability to corrosion. Furthermore, the weldless securement of the bearing can resist axial loads applied by a deflection mechanism contained within the bearing housing to provide a mechanically robust biostimulator transport system.

Figure 1:
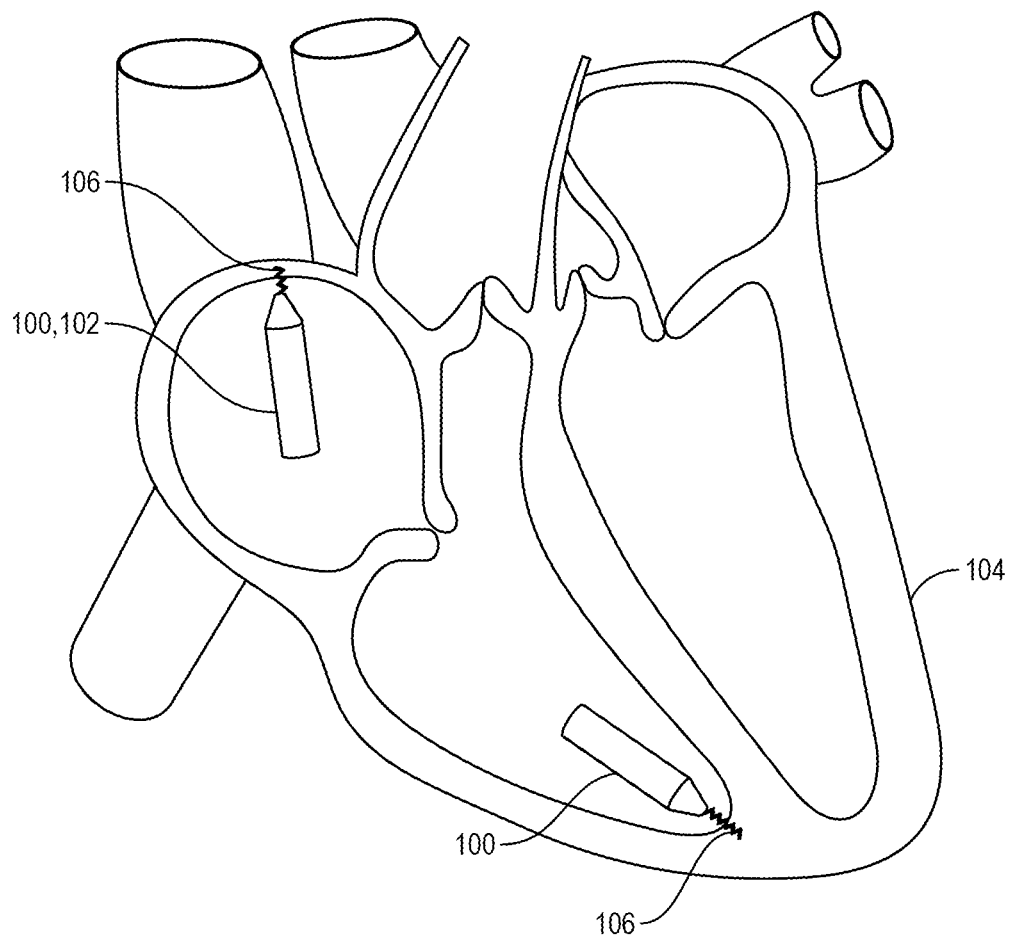
FIG. 1 is a diagrammatic medial-lateral cross section of a patient heart illustrating an example implantation of biostimulators in the patient heart, in accordance with an embodiment.

Referring to FIG. 1, a diagrammatic medial-lateral cross section of a patient heart illustrating an example implantation of biostimulators in the patient heart is shown in accordance with an embodiment. A cardiac pacing system includes one or more biostimulators 100. The biostimulators 100 can be implanted in the patient heart 104, and can be leadless, and thus may be leadless cardiac pacemakers 102. Each biostimulator 100 can be placed in a cardiac chamber, such as a right atrium and/or right ventricle of the patient heart 104, or attached to an inside or outside of the cardiac chamber. Attachment of the biostimulator 100 to the cardiac tissue can be accomplished via one or more fixation elements 106, such as helical anchors. In a particular embodiment, the leadless cardiac pacemaker 102 can use two or more electrodes located on or within a housing of the leadless cardiac pacemaker 102 for pacing the cardiac chamber upon receiving a triggering signal from internal circuitry and/or from at least one other device within the body.

Figure 2:
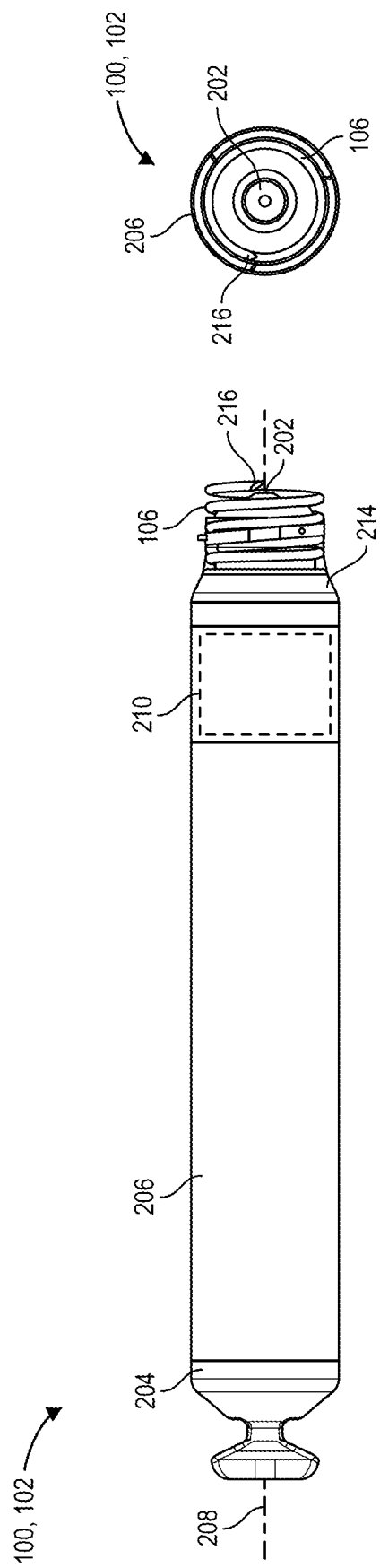
FIGS. 2A-2B are, respectively, side and end views of a biostimulator, in accordance with an embodiment.

Referring to FIG. 2A, a side view of a biostimulator is shown in accordance with an embodiment. The biostimulator 100 can be a leadless cardiac pacemaker 102 that can perform cardiac pacing and that has many of the advantages of conventional cardiac pacemakers while extending performance, functionality, and operating characteristics. The biostimulator 100 can have two or more electrodes, e.g., a distal electrode 202 and a proximal electrode 204, located within, on, or near a housing 206 of the biostimulator 100. In an embodiment, one or more of the fixation elements 106 forms a portion of the distal electrode 202. The electrodes can deliver pacing pulses to muscle of the cardiac chamber, and optionally, can sense electrical activity from the muscle. The electrodes may also communicate bidirectionally with at least one other device within or outside the body.

In an embodiment, the housing 206 has a longitudinal axis 208, and the distal electrode 202 can be a distal pacing electrode mounted on the housing 206 along the longitudinal axis 208. The housing 206 can contain a primary battery to provide power for pacing, sensing, and communication, which may include, for example bidirectional communication. The housing 206 can optionally contain an electronics compartment 210 to hold circuitry adapted for different functionality. For example, the electronics compartment 210 can contain circuits for sensing cardiac activity from the electrodes, circuits for receiving information from at least one other device via the electrodes, circuits for generating pacing pulses for delivery via the electrodes, or other circuitry. The electronics compartment 210 may contain circuits for transmitting information to at least one other device via the electrodes and can optionally contain circuits for monitoring device health. The circuit of the biostimulator 100 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

Leadless pacemakers or other leadless biostimulators 100 can be fixed to an intracardial implant site by one or more actively engaging mechanism or fixation mechanism, such as a screw or helical member that screws into the myocardium. In an embodiment, the biostimulator 100 includes the fixation element 106 coupled to the housing 206. The fixation element 106 can be a helical element to screw into target tissue. More particularly, the fixation element 106 can extend helically from a flange 214 of the biostimulator 100, which is mounted on the housing 206, to a distal tip at a helix distal end 216.

Referring to FIG. 2B, an end view of a biostimulator is shown in accordance with an embodiment. The helix distal end 216 can be located distal to the distal electrode 202 (a centrally located electrode). Accordingly, when the biostimulator 100 contacts the target tissue, the distal tip can pierce the tissue and the housing 206 can be rotated to screw the outer fixation element 106 into the target tissue to pull the distal electrode 202 into contact with the tissue.

Leadless pacemakers or other leadless biostimulators 100 can be delivered to and retrieved from a patient using a transport system, as described below. In some implementations, the transport system is a delivery system for delivering the leadless pacemaker to the target tissue. In some implementations, the transport system is a retrieval system for retrieving the leadless pacemaker from the target tissue.

Figure 3:
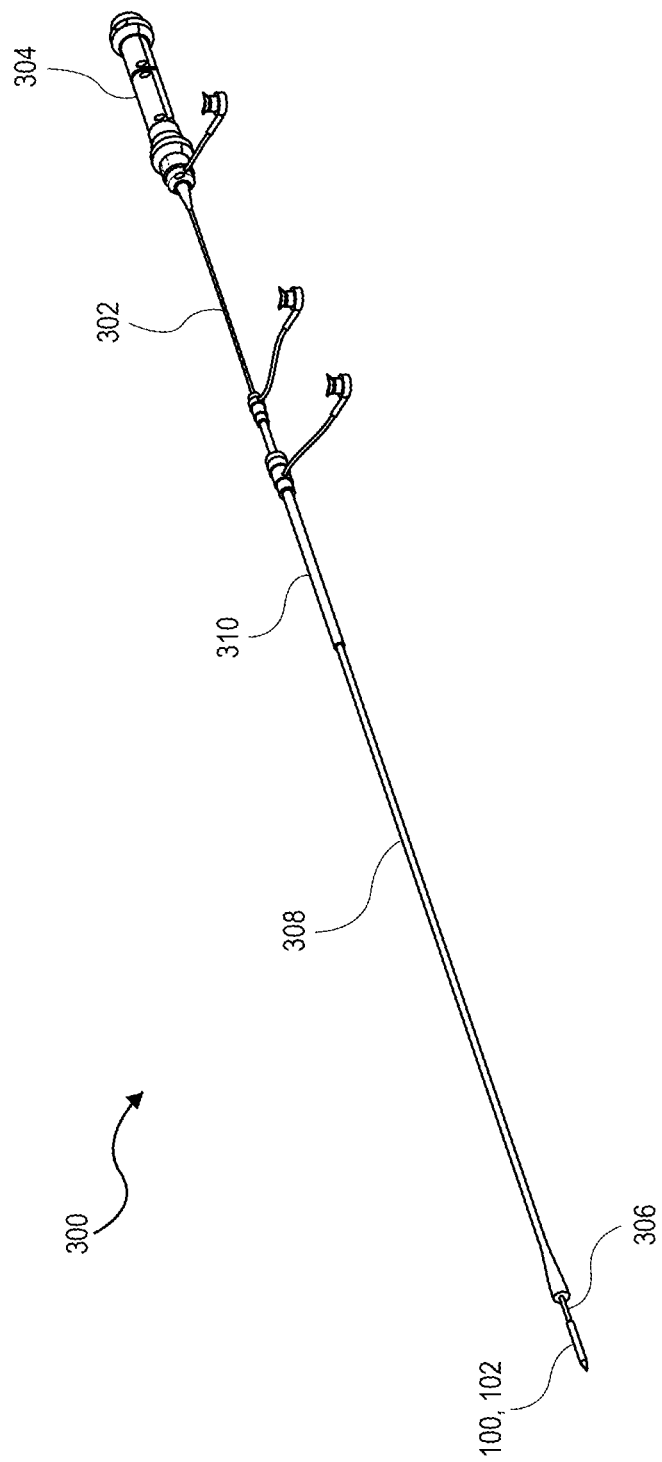
FIG. 3 is a perspective view of a biostimulator transport system, in accordance with an embodiment.

Referring to FIG. 3, a perspective view of a biostimulator transport system is shown in accordance with an embodiment. A biostimulator transport system 300 may be used for delivery and/or retrieval of a biostimulator 100, e.g., a leadless cardiac pacemaker 102, into or from a patient. The biostimulator transport system 300 can include an elongated catheter 302 extending distally from a handle 304 to a distal end 306. The elongated catheter 302 can be a deflectable catheter, and an operator can use the handle 304 to steer the distal end 306 in the patient. In an embodiment, the biostimulator transport system 300 includes a guide catheter 308 mounted on the elongated catheter 302. The guide catheter 308 can be slidably disposed on the elongated catheter 302 such that a distal portion of the guide catheter 308 can slide distally over the distal end 306 of the elongated catheter 302 and/or the biostimulator 100. Similarly, the biostimulator transport system 300 can include an introducer hub assembly 310 mounted on the guide catheter 308. The introducer hub assembly 310 can be slidably disposed on the guide catheter 308 such that a distal portion of the introducer hub assembly 310 can slide distally over the distal end 306 of the elongated catheter 302 and/or the distal portion of the guide catheter 308. More particularly, the introducer hub assembly 310 can be inserted into an access sheath to gain access to the patient vasculature, and after access is established, the distal portion of the guide catheter 308 and/or the distal end 306 of the elongated catheter 302 can be advanced through the access sheath into the patient.

The distal end 306 of the elongated catheter 302 may be selectively connectable to the biostimulator 100. More particularly, the biostimulator 100 can be mounted on the distal end 306 of the elongated catheter 302. The biostimulator 100 can be protected by a protective pacemaker sheath of the distal portion of the guide catheter 308 during delivery and/or retrieval of the biostimulator 100 from the patient. Accordingly, the biostimulator 100 can be advanced into the patient along with the distal end 306.

The leadless pacemaker system can be used to implant one or more biostimulators 100 within an atrium and/or a ventricle of a heart 104 of the patient. Implantation of each biostimulator 100 may be achieved, in part, by endocardial insertion of the biostimulators 100. For example, the elongated catheter 302 of the leadless pacemaker system can include a torque shaft that is torqueable and can be used to rotate the biostimulator 100 in a first direction, e.g., clockwise. Rotating the biostimulator 100 when the fixation element 106 is in contact with the heart tissue can cause the fixation element 106 to screw into the heart tissue and affix the biostimulator 100 to the heart tissue. Similarly, removal and retrieval of the biostimulators 100 may be accomplished endocardially. For example, the torque shaft of the elongated catheter 302 can be rotated in a second direction, e.g., counterclockwise, to disengage the biostimulator 100 from the heart tissue. Accordingly, delivery and retrieval systems having a structure similar to that shown in FIG. 3 may be used to deliver and/or retrieve the biostimulator 100 from a target anatomy.

Figure 4:
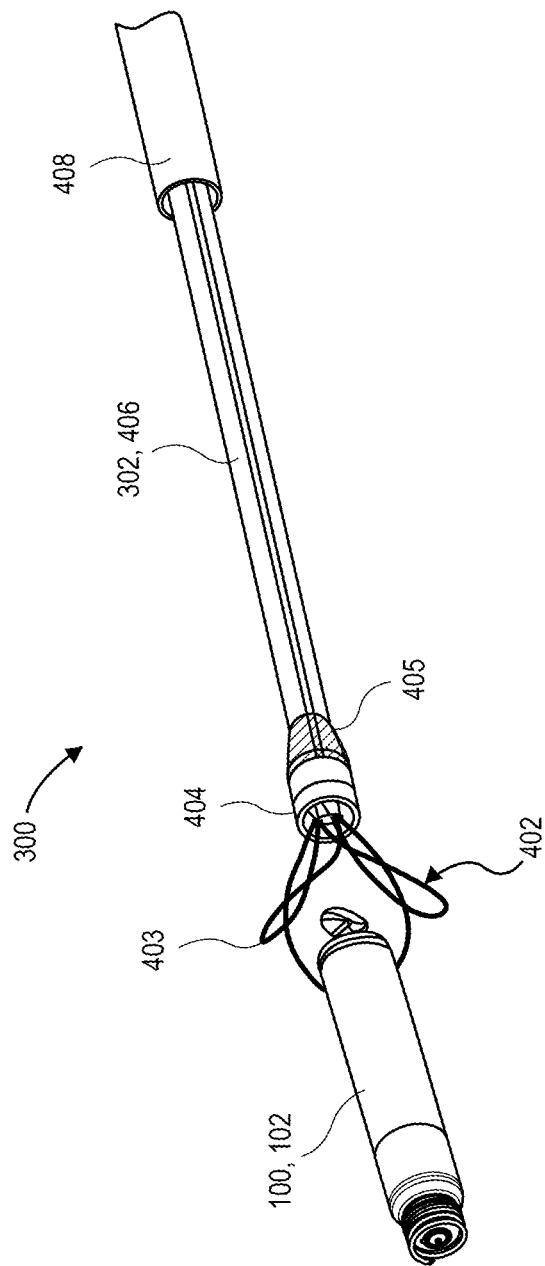
FIG. 4 is a perspective view of a distal portion of a biostimulator retrieval system prior to attaching to a biostimulator, in accordance with an embodiment.

Referring to FIG. 4, a perspective view of a distal portion of a biostimulator retrieval system prior to attaching to a biostimulator is shown in accordance with an embodiment. The view is a close-up view of one embodiment of a distal portion of the biostimulator transport system 300 shown in FIG. 3 as used for retrieval of a leadless pacemaker. Accordingly, the retrieval system can include features to engage the leadless cardiac pacemaker 102 to facilitate capturing and unscrewing the biostimulator 100 from the target tissue.

The distal portion of the retrieval catheter can include a snare 402 configured to grasp a biostimulator 100 or other medical device. The snare 402 can include at least one loop 403, e.g., a wire loop, extending from the elongated catheter 302. As the snare 402 is advanced distally out of the biostimulator transport system 300 from a docking cap 404, the loops 403 can expand in size to aid a user in positioning the snare 402 around or in proximity to the biostimulator 100 to be retrieved. In some implementations, as in FIG. 4, the snare 402 can include multiple loops 403, such as three loops. However, any number of loops 403 can be used as long as the elongated catheter 302 contains sufficient volume to accommodate the loops.

The distal portion of the retrieval catheter can include the docking cap 404 configured to allow docking of the leadless cardiac pacemaker 102 with the biostimulator transport system 300 after engaging the pacemaker with the snare 402, and a bearing housing 405 that contains a bearing to support the docking cap 404 and to allow relative rotation between the docking cap 404 and the bearing housing 405 during torque transmission. More particularly, the bearing housing 405 can be mounted on an outer catheter 406 of the elongated catheter 302, and the docking cap 404 can be mounted on a torque shaft (hidden within the outer catheter 406) of the elongated catheter 302. A user can transmit torque through the torque shaft via handle controls to rotate the docking cap 404 relative to the bearing housing 405. More particularly, the torque shaft can extend through the length of the catheter to a torque knob on the handle 304, or another rotatable portion of the handle 304, which is coupled to the torque shaft. Rotation or actuation of the torque knob rotates the torque shaft, thereby rotating the docking cap 404 at the end of the retrieval catheter. In some implementations, the docking cap 404 can include a keyed portion or interference feature so as to apply additional torque to the pacemaker when rotating the biostimulator 100. A protective sheath 408 of the guide catheter 308 can be positioned along the outer catheter 406, and can be advanced or retracted to cover or expose the docking cap 404 and the leadless pacemaker.

During retrieval, the biostimulator transport system 300 can be navigated through the patient to the implant site. The snare 402 can be placed over a retrieval feature, e.g., a handle 304 or hook feature on the biostimulator 100, and the loops 403 of the snare 402 can be reduced in size, thereby grasping or locking onto the retrieval feature of the pacemaker. Following capture and locking of the snare 402 with the leadless pacemaker, the biostimulator 100 may be docked within the docking cap 404. More particularly, the attachment feature of the biostimulator 100 can be pulled into a docking cavity of the docking cap 404. In some implementations, the docking cap 404 can include a key or interference feature configured to mate with and engage a corresponding key or feature on the pacemaker. In some implementations, the key or slot on the docking cap 404 can match a unique shape or feature of the retrieval feature of the pacemaker. Because the key or slot on or in the docking cap 404 can mate with and engage the key or slot on the pacemaker, the retrieval catheter can be configured to apply torque to the pacemaker to unscrew and remove the pacemaker from tissue.

Figure 5:
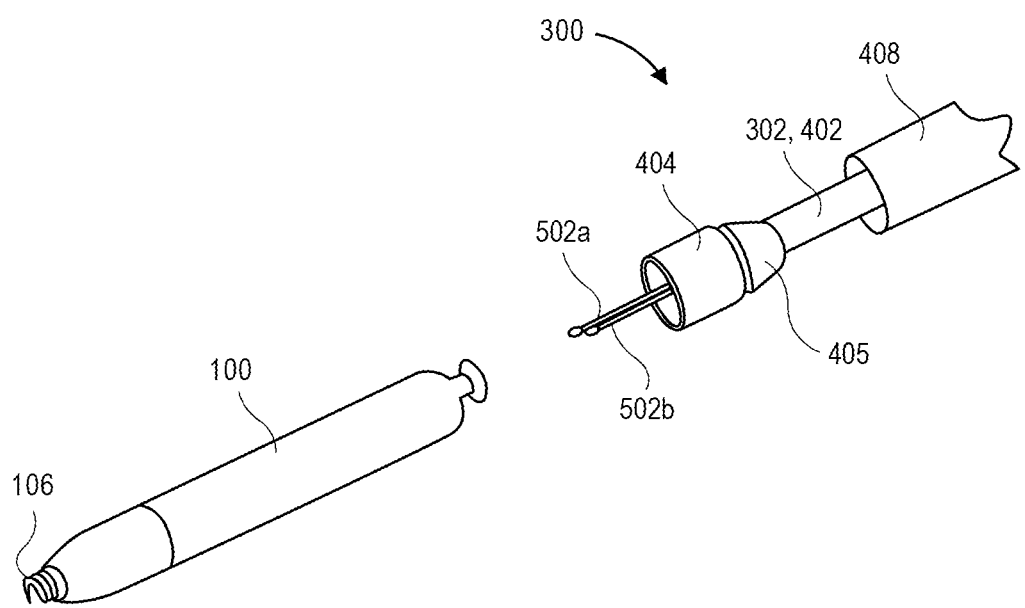
FIG. 5 is a perspective view of a distal portion of a biostimulator delivery system prior to attaching to a biostimulator, in accordance with an embodiment.

Referring to FIG. 5, a perspective view of a distal portion of a biostimulator delivery system prior to attaching to a biostimulator is shown in accordance with an embodiment. The view is a close-up view of one embodiment of a distal portion of the biostimulator transport system 300 shown in FIG. 3 as used for delivery of a leadless pacemaker. Accordingly, the delivery system can include features to engage the leadless pacemaker to allow screwing the biostimulator 100 into the target tissue.

Similar to the retrieval system, the delivery system can include the docking cap 404 having a key configured to engage the leadless pacemaker and apply torque to screw the fixation element 106 into the target tissue. The delivery system may also include the elongated catheter 302 having the torque shaft on which the docking cap 404 is mounted, and the outer catheter 406 on which the bearing housing 405 is mounted. The protective sheath 408 of the guide catheter 308 can be positioned along the outer catheter 406, and can be advanced or retracted to cover or expose the docking cap 404 and the leadless pacemaker.

In an embodiment, the delivery system includes tethers 502*a*, 502*b* configured to engage a docking feature on the biostimulator 100. The tethers 502 can include wires, shafts, tubes, cords, ropes, strings, or other similar structures that can extend throughout the elongated catheter 302. In some implementations, the tethers 502 include a shape memory material, such as nitinol. In other implementations, the tethers 502 include stainless steel wires or braids.

Delivery of the biostimulator 100 can be accomplished by tethering the biostimulator 100 to the biostimulator transport system 300. The tethers 502 can include distal features, for example, features on the tethers 502 that protrude radially from the tether 502, such as bumps, spheres, cylinders, rectangles, or other similar shapes extending outwards from the tethers 502. Generally, the distal features have a cross-sectional diameter larger than the cross sectional diameter of the tethers 502. In one embodiment, the distal feature on the tether 502*a* can be advanced further from the catheter than the distal feature on the tether 502*b*, so that when the tethers 502 are pushed together, the distal feature on the tether 502*b* rests against the tether 502*a*. This causes the combined cross sectional dimension of the distal feature and the tether 502 to be less than if the distal features were lined up side by side.

When the tethers 502 and distal features are in the un-aligned configuration, the cross sectional diameter of the distal features is reduced since the distal features are not positioned side by side. The tether distal features can then be advanced in this un-aligned configuration through a hole of an attachment feature of the leadless pacemaker (not shown). In this implementation, the diameter of the hole can be sufficiently large enough to allow the distal features of the tethers 502 to pass when in the un-aligned configuration. Upon passing the distal features through the hole, the length of the tethers 502 can then be adjusted to align the distal features in the side by side configuration. When the distal features are positioned side by side, the combined cross-sectional diameter of the distal features becomes larger than the diameter of the hole, which essentially locks the tethers and distal features in the attachment feature, and prevents the distal features from being able to pass proximally through the hole.

When the tethers 502 are locked to the biostimulator 100, the tethers 502 can be retracted to dock the biostimulator 100 to the docking cap 404. More particularly, the attachment feature of the biostimulator 100 can be pulled into a docking cavity of the docking cap 404. The docking cap 404 of the delivery system can include a torque slot (not shown) sized and configured to mate with the attachment feature of the biostimulator 100, which is disposed on a proximal end of the pacemaker. It should be appreciated that the attachment feature and the torque slot can include any number of shapes, such as square, rectangle, triangle, pentagon, hexagon, cross, "X", etc., so long as the attachment feature fits within and can have rotational torque applied to it by the torque slot. When the distal end 306 of the biostimulator transport system 300 is navigated through the patient to a delivery site, the torque slot can be rotated via rotation of the torque shaft, which runs the length of the elongated catheter 302 and into the handle 304 (not shown). Accordingly, the biostimulator 100 can be screwed into the cardiac tissue at the delivery site. The tethers 502 can be misaligned to release the biostimulator 100 from the biostimulator transport system 300 at the delivery site.

Figure 10:
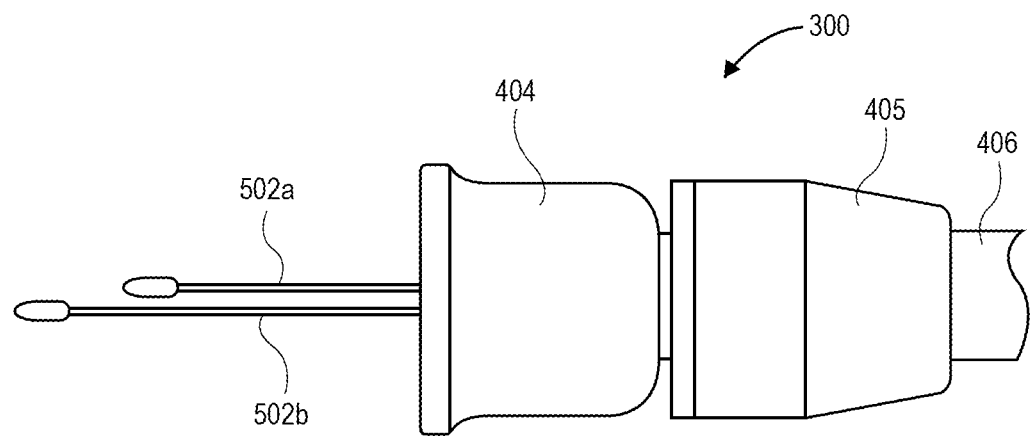
FIG. 10 is a side view of a distal portion of a biostimulator delivery system, in accordance with an embodiment.
Figure 11:
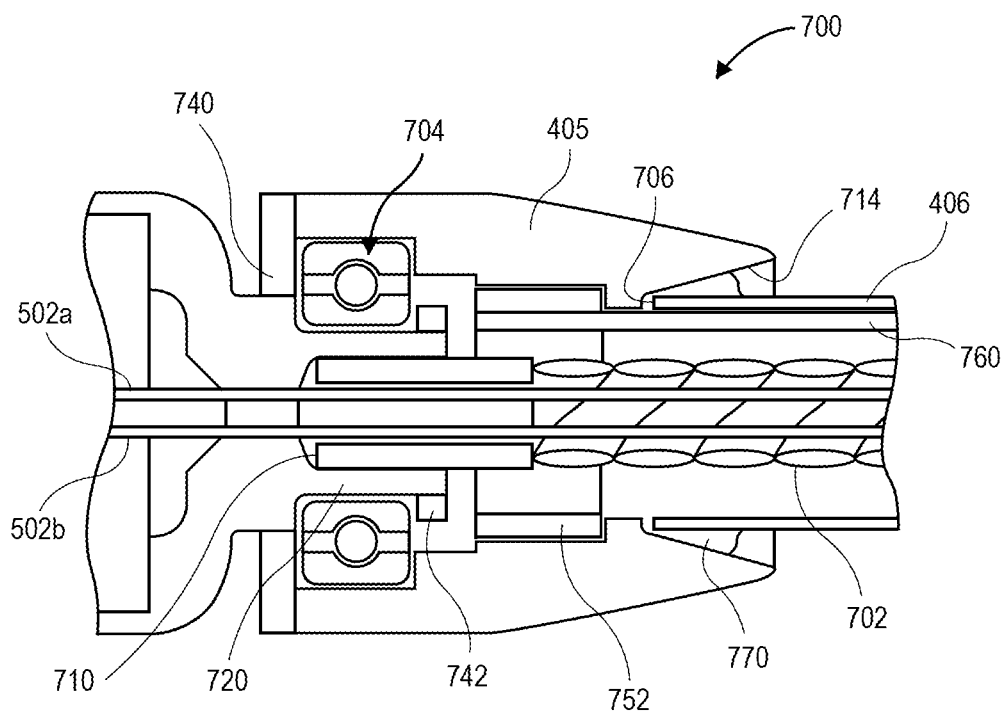
FIG. 11 is a cross-sectional view of the distal portion of the biostimulator delivery system of FIG. 10, in accordance with an embodiment.

Having discussed the biostimulator transport systems generally, the distal portion of the biostimulator transport system 300 shall now be described in greater detail with respect to both a retrieval system and a delivery system. It will be appreciated that features described for one type of transport system, e.g., a retrieval system as shown in FIGS. 6-9, may be incorporated in another type of transport system, e.g., a delivery system as shown in FIGS. 10-11.

Figure 6:
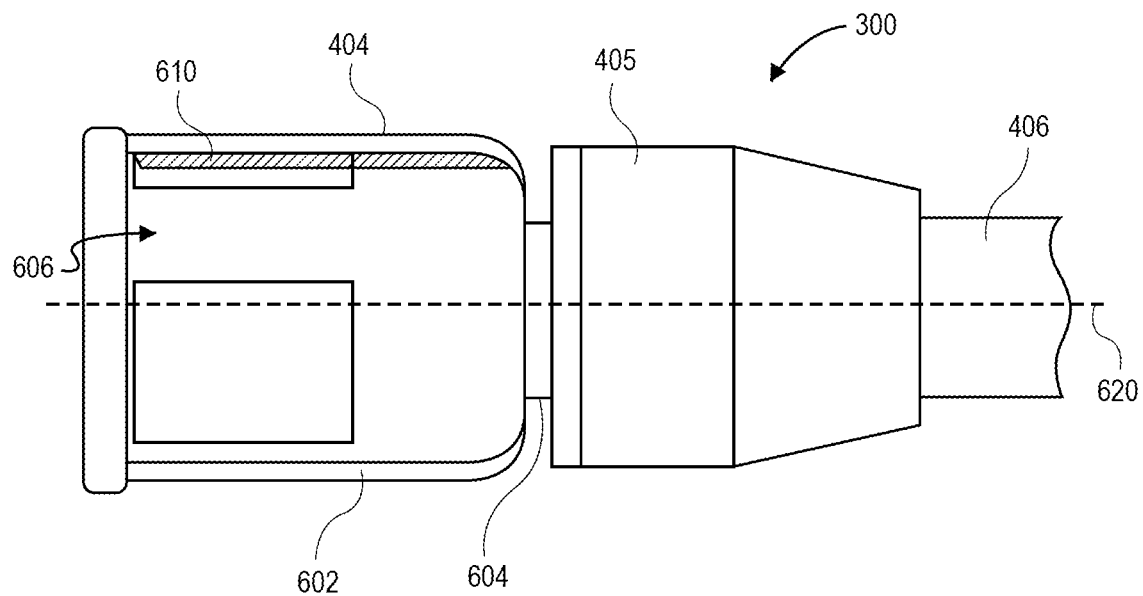
FIG. 6 is a side view of a distal portion of a biostimulator retrieval system, in accordance with an embodiment.

Referring to FIG. 6, a side view of a distal portion of a biostimulator retrieval system is shown in accordance with an embodiment. The biostimulator transport system 300 used to retrieve the leadless cardiac pacemaker 102 includes the bearing housing 405 mounted on the outer catheter 406. The bearing housing 405 has an outer surface surrounding the components contained within the housing 206, such as a bearing as described below. The bearing interconnects the bearing housing 405 with the docking cap 404. More particularly, a neck of the docking cap 404 is interconnected with the bearing housing 405, as described below, and the bearing allows the docking cap 404 to rotate about a central axis 620 relative to the bearing housing 405.

The docking cap 404 can include a distal cup portion 602 that extends distally from the bearing housing 405. The distal cup 602 can include a docking cavity 606, which may be a generally cylindrically-shaped void within the distal cup 602. The docking cavity 606 can be sized and configured to receive the attachment feature of the biostimulator 100. Furthermore, as described above, a torque key feature 610 may be located within the docking cavity 606 to engage the attachment feature and transmit torque to the biostimulator 100. In an embodiment, a base 604 of the docking cap 404 extends between the distal cup 602 and the bearing housing 405, and the torque is transmitted to the distal cup 602 through the base 604.

Figure 7:
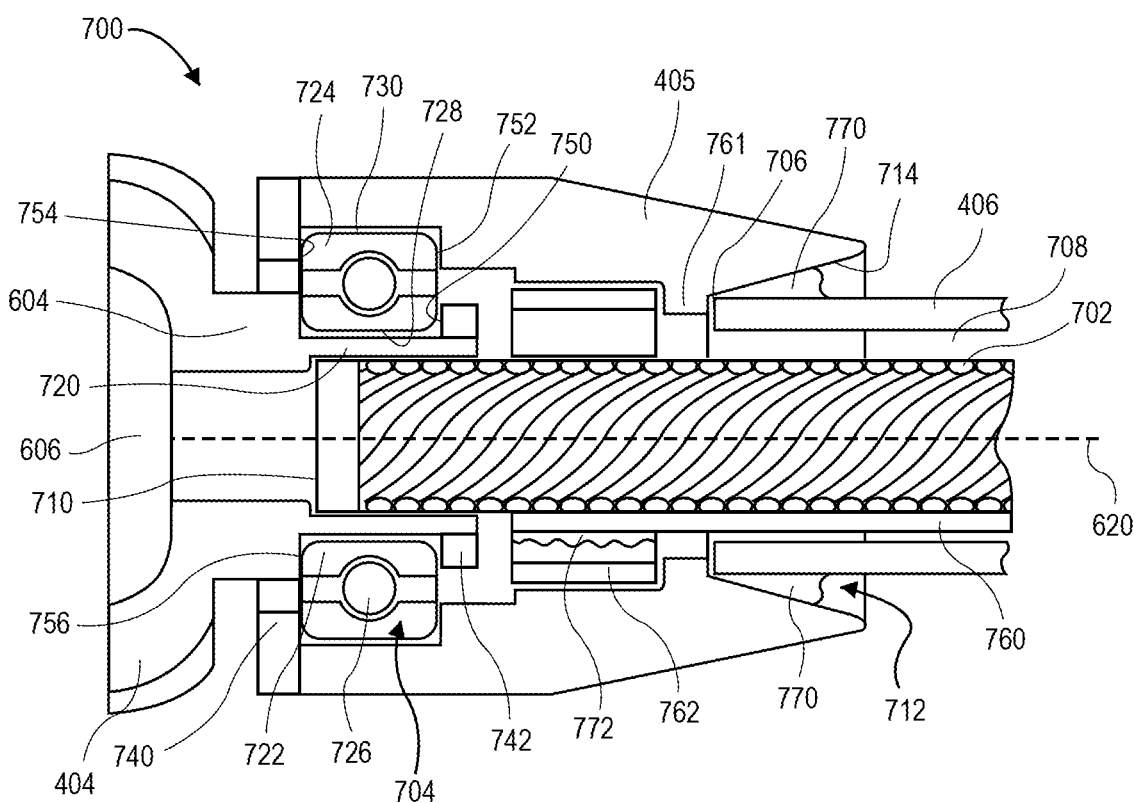
FIG. 7 is a cross-sectional view of the distal portion of the biostimulator retrieval system of FIG. 6, in accordance with an embodiment.

Referring to FIG. 7, a cross-sectional view of the distal portion of the biostimulator retrieval system of FIG. 6 is shown in accordance with an embodiment. The distal portion can include a torque shaft assembly 700 of the biostimulator transport system 300. The torque shaft assembly 700 can include a torque shaft 702 connected to the docking cap 404, and a bearing 704 interconnecting the docking cap 404 to the bearing housing 405. As described below, the torque shaft assembly 700 can also include a pull ring assembly to impart a deflection load to the outer catheter 406 via the bearing housing 405. In an embodiment, the connections between the bearing 704, the docking cap 404, and the bearing housing 405 are weldless. More particularly, the bearing housing 405 and the docking cap 404 can retain the bearing 704 without weld joints. Eliminating bearing welds can enhance mechanical performance of the bearing 704, decrease weld failure rates of the transport system, and enhance corrosion performance of the metallic components of the distal portion.

In an embodiment, the outer catheter 406 of the transport system extends along the central axis 620 from the handle 304 to a distal catheter end 706. More particularly, the outer catheter 406 has an inner lumen 708 that extends from the proximal catheter end to the distal catheter end 706 along the central axis 620. The inner lumen 708 provides a channel within which the torque shaft 702 is disposed. More particularly, the torque shaft 702 extends through the inner lumen 708 from the handle 304 to a distal shaft end 710. The distal shaft end 710 can be located distal to the distal catheter end 706. Accordingly, the torque shaft 702 can connect to the docking cap 404 at a location that is distal to a location at which the outer catheter 406 connects to the bearing housing 405.

In an embodiment, the bearing housing 405 is mounted on the distal catheter end 706. For example, the bearing housing 405 can include a proximal recess 712 to receive the distal catheter end 706 of the outer catheter 406. The proximal recess 712 can extend distally into a proximal face of the bearing housing 405. The proximal recess 712 can extend to a depth that allows a length of the outer catheter 406 to be located inside of the bearing housing 405 radially inward from a recess wall 714 that defines a lateral boundary of the proximal recess 712. In an embodiment, the recess wall 714 is a tapered wall having a proximal dimension, e.g., a cross-sectional diameter at a proximalmost location, that is greater than a distal dimension, e.g., a cross-sectional diameter at a distalmost location. The tapered recess and the proximal end of the bearing housing 405 provides a cavity to receive an adhesive. The adhesive can form a joint 770 to bond the bearing housing 405 to the outer catheter 406. In an embodiment, the adhesive is a light-activated adhesive, such as an ultraviolet light-activated adhesive. As described below, the bearing housing 405 may be formed from an opaque metal, and thus, the tapered recess allows sufficient light to penetrate axially into the adhesive joint 770 to irradiate and cure the adhesive within the proximal recess 712. Accordingly, the tapered recess allows for the formation of an effective attachment between the distal catheter end 706 and the bearing housing 405.

The docking cap 404 of the biostimulator transport system 300 can be mounted on the distal shaft end 710 of the torque shaft 702. For example, the docking cap 404 can include a neck 720 that extends proximally from the base portion 604, and the distal shaft end 710 can be inserted into a central cavity of the neck 720. More particularly, the neck 720 can be a tubular extension extending from the base 604, and the torque shaft 702 can be received within a central lumen of the tubular extension. In an embodiment the central lumen can extend entirely through the neck 720 and the base 604 into docking cavity 606. Accordingly, a lumen of the torque shaft 702 can align with the central lumen of the docking cap 404 to allow the snare 402 (not shown) to pass from the torque shaft 702 through the docking cap 404 toward the biostimulator 100 during retrieval.

The torque shaft 702 can be attached to the docking cap 404. For example, an adhesive or thermal weld can be formed between the neck 720 and an outer surface of the torque shaft 702. The docking cap 404 and the torque shaft 702 can be formed from a same material, e.g., stainless steel, and thus, a thermal weld can robustly secure the torque shaft 702 to the docking cap 404 to allow torque applied at the handle 304 to be transmitted through the torque shaft 702 to the docking cap 404. The docking cap 404 can in turn transmit torque to the biostimulator 100 to unscrew the fixation element 106 from the target tissue.

The bearing 704 can support the docking cap 404 relative to the bearing housing 405. The bearing 704 can be radially between the bearing housing 405 and the docking cap 404, and can hold the neck 720 of the docking cap 404 concentrically with respect to an internal surface of the bearing housing 405. The bearing 704 allows the docking cap 404 to rotate freely relative to the bearing housing 405. The bearing 704 can be any of several types of bearings that permit radial rotation of the docking cap 404. For example, the bearing 704 can be a plain bearing, such as a bushing formed from a smooth material, e.g., polytetrafluoroethylene (PTFE). Alternatively, the bearing 704 can be a rolling-element bearing, a jewel bearing, etc. In an embodiment, the bearing 704 is a ball bearing having an inner race 722, an outer race 724, and several balls 726 between the inner race 722 and the outer race 724 to allow the races to rotate freely relative to each other. The bearing 704 can be a roller bearing having several rollers. In any case, the bearing 704 can have an inner wall 728, e.g., an inner surface of the inner race 722, apposed to the neck 720 of the docking cap 404, and an outer wall 730, e.g., an outer surface of the outer race 724, apposed to the internal surface of the bearing housing 405.

The bearing 704 can be retained on the docking cap 404 and within the bearing housing 405 without the use of welds. It will be understood that any welds between the bearing 704 and the docking cap 404 or the bearing housing 405 may be prone to cracking under the loads applied during delivery or retrieval of the biostimulator 100. Weld strength problems may be particularly exacerbated in the case of welds between dissimilar metals. Given that the bearing 704 may be formed from a material that is different than the docking cap 404 or the bearing housing 405, it follows that any welds therebetween may have unreliable joint strength. Furthermore, welds between dissimilar materials can be susceptible to corrosion, and the welds can warp one or more of the races of the bearing 704, which may lead to reduced bearing function due to the heat affected zone formed during welding. For all of these reasons, the torque shaft assembly 700 as described herein can include the bearing 704 that is not attached to the docking cap 404 or the bearing housing 405.

The biostimulator transport system 300 can include the bearing 704 nested between retainers of the docking cap 404 and the bearing housing 405. By nesting the bearing 704 between the retainers, the bearing 704 can be secured in place without the need for attachment joints, such as welds. Accordingly, the retainers of the biostimulator transport system 300 may be weldless. In an embodiment, the bearing 704 is located axially between an outer bearing retainer 740 of the bearing housing 405 and an inner bearing retainer 742 of the docking cap 404. For example, the inner bearing retainer 742 can have a distal retainer face 750 apposed to a proximal bearing face 752 of the bearing 704, and similarly, the outer bearing retainer 740 can have a proximal retainer face 754 apposed to a distal bearing face 756. The apposed faces can be in sliding contact with each other to prevent axial movement of the bearing 704 while allowing the bearing 704 to be slidably mounted on the docking cap 404 and the bearing housing 405. More particularly, the inner wall 728 of the bearing 704 can be slidably mounted on the docking cap 404 and located distal to the inner bearing retainer 742, and the outer wall 730 of the bearing 704 can be slidably mounted within the bearing housing 405 and located proximal to the outer bearing retainer 740.

The grooves in the docking cap 404 and the bearing housing 405 that hold the outer and inner races 724, 722 of the bearing 704 can be formed in several ways. For example the outer and inner bearing retainers 740, 742 can be separate components that are attached to the docking cap 404 or the bearing housing 405 as described below with respect to FIGS. 8-9. Alternatively, the bearing retainers can be formed by deforming the docking cap 404 or the bearing housing 405. For example, a proximal end of the neck 720 can be flared outward to form the inner bearing retainer 742, or a distal end of the bearing housing 405 can be crimped, swaged, or bent inward to form the outer bearing retainer 740. In any case, an outer groove can be provided on an internal surface of the bearing housing 405 to hold the outer wall 730 of the bearing 704, and an inner groove can be provided on an external surface of the docking cap 404 to hold the inner wall 728 of the bearing 704. The grooves can therefore have respective distal and proximal retainer faces that appose the bearing surfaces. As such, the outer groove mates with the outer portion of the bearing 704 and the inner groove mates with the inner portion of the bearing 704 to retain the bearing 704 without welds that could otherwise compromise the strength or function of the bearing 704.

In an embodiment, the torque shaft assembly 700 contains a deflection mechanism that allows a user to deflect the elongated catheter 302 laterally using the handle 304 of the biostimulator transport system 300. The deflection mechanism can include a pull wire 760 that extends through the inner lumen 708 from the handle 304 into the bearing housing 405. The pull wire 760 may extend axially through the inner lumen 708 between the outer catheter 406 and the torque shaft 702. Accordingly, axial loads applied to a proximal end of the pull wire 760 at the handle 304 can cause movement of a distal end of the pull wire 760 within the bearing housing 405. The deflection mechanism may also include a pull ring 762 that is contained within the bearing housing 405 axially between the distal catheter end 706 and the bearing 704. The pull ring 762 can be connected to the pull wire 760. For example, the distal end of the pull wire 760 may be bonded to the pull ring 762 by a joint 772, e.g., a weld. Accordingly, axial loads applied to the pull wire 760 by the handle 304 can cause movement of the pull ring 762 within the bearing housing 405.

Containment of the pull ring 762 within the bearing housing 405 provides a simple design that efficiently transmits axial loads through the pull wire 760 to the bearing housing 405. For example, a proximal surface of the pull ring 762 may abut a ledge 761 on the internal surface of the bearing housing 405. More particularly, an interference fit can be provided between the pull ring 762 and the ledge 761. The interference fit allows the pull ring 762 to apply a load to the bearing retainer without a need for a weld. The weldless connection between the pull ring 762 and the bearing housing 405 allows for the pull ring 762 and the bearing housing 405 to be formed from different materials without a risk of corrosion of the components. When the pull wire 760 is pulled, the proximal surface of the pull ring 762 can press against the ledge 761. The pull wire 760 may be laterally offset from the central axis 620 of the elongated catheter 302. Thus, the pull force can be applied to the ledge 761 eccentrically such that the bearing housing 405 preferentially deflects in a direction, causing the outer catheter 406 to bend laterally in that direction.

Figure 8:
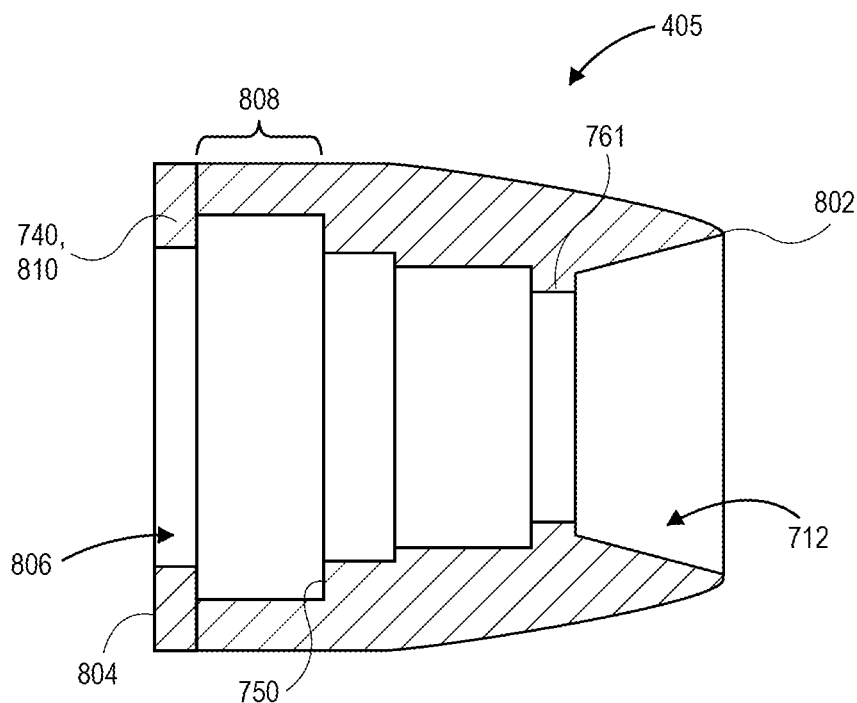
FIG. 8 is a cross-sectional view of a bearing housing of a biostimulator retrieval system, in accordance with an embodiment.

Referring to FIG. 8, a cross-sectional view of a bearing housing of a biostimulator retrieval system is shown in accordance with an embodiment. The bearing housing 405 can consolidate the bearing 704 and pull ring 762 within an internal region, e.g., a distal recess 806, that is distal to the ledge 761. By contrast, the proximal recess 712 can be proximal to the ledge 761, and can contain the distal catheter end 706 of the outer catheter 406. The distal recess 806 and the proximal recess 712 can be in communication via a hole that passes through the ledge 761 in the longitudinal direction. The hole can receive the torque shaft 702 and the pull wire 760.

In an embodiment, the bearing housing 405 has a one-piece design. The one-piece design of the bearing housing 405 does not require adhesive joints, which have been shown to be susceptible to mechanical failure in two-piece bearing housing designs. More particularly, the one-piece design of the bearing housing 405 can have a solid and continuous lateral wall that extends from a proximal housing end 802 to a distal housing end 804. The lateral wall can surround an internal cavity that includes the proximal recess 712 and the distal recess 806. The internal cavity can extend longitudinally from a proximal entrance at the proximal recess 712 to a distal entrance at the outer bearing retainer 740. The bearing housing 405 can be machined from a metal blank, such as a stainless steel blank, to provide the internal and external geometry shown in FIG. 8. For example, the internal cavity can have an internal surface distal to the ledge 761 that provides a slip fit with the pull ring 762, and an internal surface proximal to the outer bearing retainer 740 that provides a groove to receive the bearing 704. The bearing housing 405 may alternatively be molded, cast, or otherwise formed to have a one-piece design.

The groove that receives an outer portion of the bearing 704 may be formed from a combination of components. For example, the bearing housing 405 can include a distal flange 808 that extends around the outer wall 730 of the bearing 704 proximal to the distal housing end 804. The outer bearing retainer 740 can include an outer annulus 810 that is coupled to the distal flange 808 to form the groove that receives the bearing 704. In an embodiment, the outer annulus 810 is a ring or annular disk that is formed from a same material as the bearing housing 405, e.g., stainless steel. The outer annulus 810 can have an inner diameter surrounding the distal entrance to the distal recess 806, which is less than an inner diameter of the distal flange 808. The outer annulus 810 can be welded to the distal flange 808 to provide a lip distal to the groove that receives the retainer. The lip is distal to the bearing 704, when the bearing 704 is seated radially inward from the distal flange 808, and stops the bearing 704 from moving distally. Accordingly, the lip can have the proximal retainer face 754.

The distal flange 808 can include a cylindrically-shaped rim that guides and retains the bearing 704. The bearing housing 405 can have a step proximal to the distal flange 808 against which the proximal bearing face 752 is seated. More particularly, the step can include the distal retainer face 750 that apposes the bearing 704. The step in the internal surface of the bearing housing 405 can stop the bearing 704 from moving proximally. Accordingly, the outer annulus 810 and the step of the bearing housing 405 provide a weldless retainer to hold the bearing 704, e.g., the outer race 724, in place.

Figure 9:
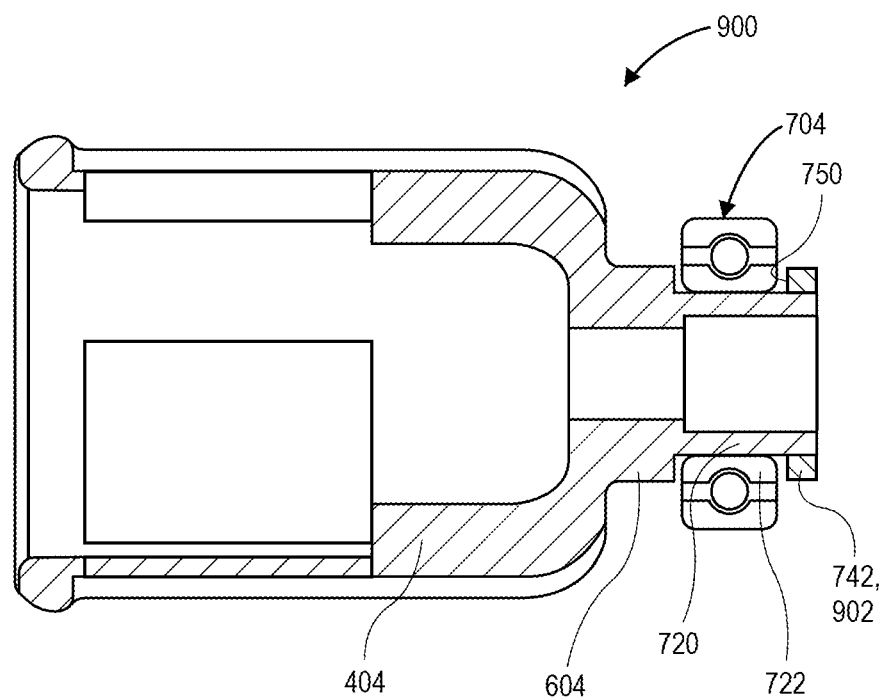
FIG. 9 is a cross-sectional view of a docking cap assembly of a biostimulator retrieval system, in accordance with an embodiment.

Referring to FIG. 9, a cross-sectional view of a docking cap assembly of a biostimulator retrieval system is shown in accordance with an embodiment. The docking cap assembly 900 includes the docking cap 404 and the bearing 704. More particularly, the bearing 704 is slidably mounted on the docking cap 404 and retained between the base 604 of the docking cap 404 and the inner bearing retainer 742. As described above, the inner bearing retainer 742 can be monolithically formed with the docking cap 404, e.g., by flaring the neck 720 of the docking cap 404 radially outward to provide the retaining groove. In an embodiment, however, the retaining groove can be formed by a combination of components.

The inner bearing retainer 742 of the biostimulator transport system 300 can include an inner annulus 902 mounted on the neck 720 of the docking cap 404. Like the outer annulus 810, the inner annulus 902 can include a ring or annular disk that is welded onto a proximal end of the neck 720. The inner annulus 902 and the neck 720 may be formed from a same material. Accordingly, when the inner annulus 902 is welded to the neck 720, a strong weld can be formed. The strength of the weld joint between the inner annulus 902 and the docking cap 404 can be rated in terms of a comparison to a weld between the bearing 704 and the docking cap 404. As described above, the bearing races and the neck 720 are typically formed from different materials, and thus, a weld between the bearing 704 and the docking cap 404 is weaker than the weld between the inner annulus 902 and the neck 720. Accordingly, a retention strength of the docking cap 404 having a retention groove can be substantially increased as compared to a weld between the bearing race and the docking cap 404. The retention groove formed between the inner annulus 902 and the base 604 of the docking cap 404 provides a weldless retainer to hold the bearing 704, e.g., the inner race 722, in place.

Referring to FIGS. 10 and 11, various views of a distal portion of a biostimulator delivery system are shown in accordance with an embodiment. The biostimulator delivery system is another type of the biostimulator transport system 300 described above. Certain features may differ between alternative types of biostimulator transport systems 300. For example, referring to FIGS. 10-11, the biostimulator delivery system may include the tethers 502 having the distal features to engage the attachment feature of the biostimulator 100, as described above. The tethers 502 can extend axially through the central lumen of the torque shaft 702 from the handle 304 into a surrounding environment distal to the docking cap 404. Many features of alternative types of biostimulator transport systems 300, however, may be the same. For example, the features described above with respect to the biostimulator retrieval system in FIGS. 6-9 may be similarly incorporated into the biostimulator delivery system of FIGS. 10-11. In the interest of brevity, like features are indicated by the reference numerals in FIGS. 10-11. It will be appreciated that the descriptions provided above with respect to FIGS. 6-9 also apply to FIGS. 10-11. Accordingly, such features may be claimed as part of a biostimulator retrieval system or a biostimulator delivery system, each of which is a type of the biostimulator transport system 300.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A docking cap assembly, comprising:
a docking cap having a docking cavity to receive an attachment feature of a biostimulator, and a neck having a radially outward surface, wherein the docking cap has an inner bearing retainer having a distal retainer face; and
a bearing slidably mounted on the radially outward surface of the neck, wherein the bearing has a proximal bearing face in sliding contact with the distal retainer face.

2. The docking cap assembly of claim 1, wherein the inner bearing retainer is proximal to the bearing.

3. The docking cap assembly of claim 2, wherein the distal retainer face is apposed to the proximal bearing face of the bearing.

4. The docking cap assembly of claim 2, wherein the inner bearing retainer includes an inner annulus mounted on the neck.

5. The docking cap assembly of claim 4, wherein the inner annulus and the neck are of a same material, and wherein the inner annulus is welded to the neck.

6. The docking cap assembly of claim 1, wherein the bearing includes an inner race slidably mounted on the neck, an outer race, and a plurality of rollers between the inner race and the outer race.

7. The docking cap assembly of claim 6, wherein the rollers include balls.

8. The docking cap assembly of claim 1, wherein the bearing is not attached to the neck.

9. A torque shaft assembly, comprising:
a torque shaft having a distal shaft end;
a docking cap having a docking cavity to receive an attachment feature of a biostimulator, the docking cap mounted on the distal shaft end and having a neck having a radially outward surface, wherein the docking cap has an inner bearing retainer having a distal retainer face; and
a bearing slidably mounted on the radially outward surface of the neck, wherein the bearing has a proximal bearing face in sliding contact with the distal retainer face.

10. The torque shaft assembly of claim 9, wherein the distal shaft end is located in a central lumen of the neck of the docking cap.

11. The torque shaft assembly of claim 9, wherein the torque shaft is attached to the docking cap.

12. A biostimulator transport system, comprising:
an outer catheter having a distal catheter end and an inner lumen;
a torque shaft extending through the inner lumen to a distal shaft end;
a bearing housing mounted on the distal catheter end, wherein the bearing housing includes a proximal recess to receive the distal catheter end, and wherein the proximal recess includes a tapered wall;
a docking cap having a docking cavity to receive an attachment feature of a biostimulator, the docking cap mounted on the distal shaft end and having a neck having a radially outward surface, wherein the docking cap has an inner bearing retainer having a distal retainer face; and
a bearing radially between the bearing housing and the docking cap, wherein the bearing is slidably mounted on the radially outward surface of the neck, and wherein the bearing has a proximal bearing face in sliding contact with the distal retainer face.

13. The biostimulator transport system of claim 12, wherein the bearing housing includes an outer bearing retainer, and wherein the bearing includes an outer wall located proximal to the outer bearing retainer and an inner wall located distal to the inner bearing retainer.

14. The biostimulator transport system of claim 13, wherein the outer bearing retainer has a proximal retainer face apposed to a distal bearing face of the bearing.

15. The biostimulator transport system of claim 14, wherein the proximal retainer face is in sliding contact with the distal bearing face.

16. The biostimulator transport system of claim 13, wherein the tapered wall has a cross-sectional dimension that narrows in a distal direction.

17. The biostimulator transport system of claim 16 further comprising an adhesive joint between the tapered wall and the outer catheter.

18. The biostimulator transport system of claim 17, wherein the adhesive joint includes a light-activated adhesive.

19. The biostimulator transport system of claim 13 further comprising a pull ring assembly including a pull ring contained within the bearing housing axially between the distal catheter end and the bearing.

* * * * *